(12) United States Patent
Hsu

(10) Patent No.: US 12,420,319 B2
(45) Date of Patent: Sep. 23, 2025

(54) BIODEGRADABLE COMPOSITE AND PRODUCT CONTAINING BIODEGRADABLE COMPOSITE

(71) Applicants: Chung-King Hsu, Taipei (TW); Jui-Tsai Wang, Taipei (TW); Shu-Tang Chang, Taichung (TW); Hung-Ching Chang, Changhua County (TW)

(72) Inventor: Chung-King Hsu, Taipei (TW)

(73) Assignees: Chung-King Hsu, Taipei (TW); Jui-Tsai Wang, Taipei (TW); Shu-Tang Chang, Taichung (TW); Hung-Ching Chang, Changhua (TW)

( * ) Notice: Subject to any disclaimer, the term of this patent is extended or adjusted under 35 U.S.C. 154(b) by 1010 days.

(21) Appl. No.: 17/379,791

(22) Filed: Jul. 19, 2021

(65) Prior Publication Data

US 2022/0339681 A1 Oct. 27, 2022

(30) Foreign Application Priority Data

Apr. 22, 2021 (TW) ................................ 110114453

(51) Int. Cl.
| | |
|---|---|
| B09B 3/00 | (2022.01) |
| B09B 101/20 | (2022.01) |
| C05F 9/04 | (2006.01) |
| C05F 11/08 | (2006.01) |
| C08L 67/04 | (2006.01) |
| C12N 1/20 | (2006.01) |
| D21H 17/00 | (2006.01) |
| D21H 21/14 | (2006.01) |
| D21H 27/00 | (2006.01) |

(52) U.S. Cl.
CPC .................. *B09B 3/00* (2013.01); *C05F 9/04* (2013.01); *C05F 11/08* (2013.01); *C08L 67/04* (2013.01); *D21H 17/005* (2013.01); *D21H 21/14* (2013.01); *D21H 27/00* (2013.01); *B09B 2101/20* (2022.01); *C08L 2201/06* (2013.01); *C12N 1/20* (2013.01); *Y02W 30/40* (2015.05)

(58) Field of Classification Search
CPC ....... A61L 9/014; B09B 2101/20; B09B 3/00; C05F 11/08; C05F 17/10; C05F 17/20; C05F 17/80; C05F 9/00; C05F 9/02; C05F 9/04; C08L 2201/06; C08L 67/04; D21H 17/005; D21H 21/14; D21H 27/00; Y02W 30/40

See application file for complete search history.

(56) References Cited

U.S. PATENT DOCUMENTS

| | | | | |
|---|---|---|---|---|
| 2010/0209988 A1* | 8/2010 | Hutchings | ................. | C12P 1/04 435/177 |
| 2012/0306189 A1* | 12/2012 | Stewart | ................ | G06K 19/086 283/67 |
| 2015/0045215 A1* | 2/2015 | Devine | ................... | C05F 17/80 424/76.5 |
| 2017/0259976 A1* | 9/2017 | Lee | ........................ | B65D 65/46 |
| 2018/0142073 A1 | 5/2018 | Wu et al. | | |

FOREIGN PATENT DOCUMENTS

| | | |
|---|---|---|
| AU | 2021204408 A1 | 11/2022 |
| CN | 102584370 A | 7/2012 |
| CN | 104245635 A | 12/2014 |
| CN | 105733975 A | 7/2016 |
| CN | 106380240 A | 2/2017 |
| CN | 106721480 A | 5/2017 |
| CN | 107779412 A | 3/2018 |
| CN | 107954774 A | 4/2018 |
| CN | 110204376 A | 9/2019 |
| CN | 110214621 A | 9/2019 |
| CN | 111517870 A | 8/2020 |
| CN | 112174714 A | 1/2021 |
| CN | 112521188 A | 3/2021 |
| JP | H08157288 A | 6/1996 |
| JP | 2002338381 A | 11/2002 |
| JP | 2003009848 A | 1/2003 |
| JP | 2005323540 A | 11/2005 |
| JP | 2014118497 A | 6/2014 |
| WO | 0222730 A1 | 3/2002 |
| WO | 2007114324 A1 | 10/2007 |
| WO | 2014108937 A1 | 7/2014 |

OTHER PUBLICATIONS

Search Report for CN2021104348095, Issued on Aug. 29, 2023, Total of 3 page.
English Abstract for CN107954774A, Total of 1 page.
English Abstract for CN111517870A, Total of 1 page.
English Abstract for CN112521188A, Total of 1 page.
Search report for TW110114453, Issued on Oct. 15, 2021, Total of 1 page.
English abstract for CN104245635, Total of 1 page.
English abstract for WO0222730, Total of 1 page.
English abstract for WO2014108937, Total of 1 page.
Communication pursuant to Article 94(3) EPC for EP Application No. 21185273.6, Issued Nov. 21, 2024, Total of 6 pages.
Substantive Examination result for VN Application No. 1202104536, Issued Jan. 14, 2025, Total of 4 pages.
Examination report No. 1 for AU Application No. 2021204408, Issued Oct. 26, 2022, Total of 8 pages.

(Continued)

*Primary Examiner* — Hai Vo
(74) *Attorney, Agent, or Firm* — Apex Juris, pllc; Hilde M. L. Coeckx

(57) ABSTRACT

A biodegradable composite includes an organic matter and a porous material, wherein the organic matter has viable bacteria, and a total plate count of the organic matter is greater than or equal to $10^4$ CFU/g. The organic matter accounts for 40% to 80% of a weight of the biodegradable composite. The porous material accounts for 20% to 60% of the weight of the biodegradable composite. The biodegradable composite could instantly remove unpleasant odor and accelerate a decomposition process to form compost. A product containing the biodegradable composite is provided as well.

4 Claims, 1 Drawing Sheet

(56) References Cited

OTHER PUBLICATIONS

Search Report for SG Application No. 10202107477U, Issued Feb. 14, 2014, Total of 3 pages.
Office Action for JP Application No. 2021-101231, Issued Jun. 7, 2022, Total of 4 pages.

* cited by examiner

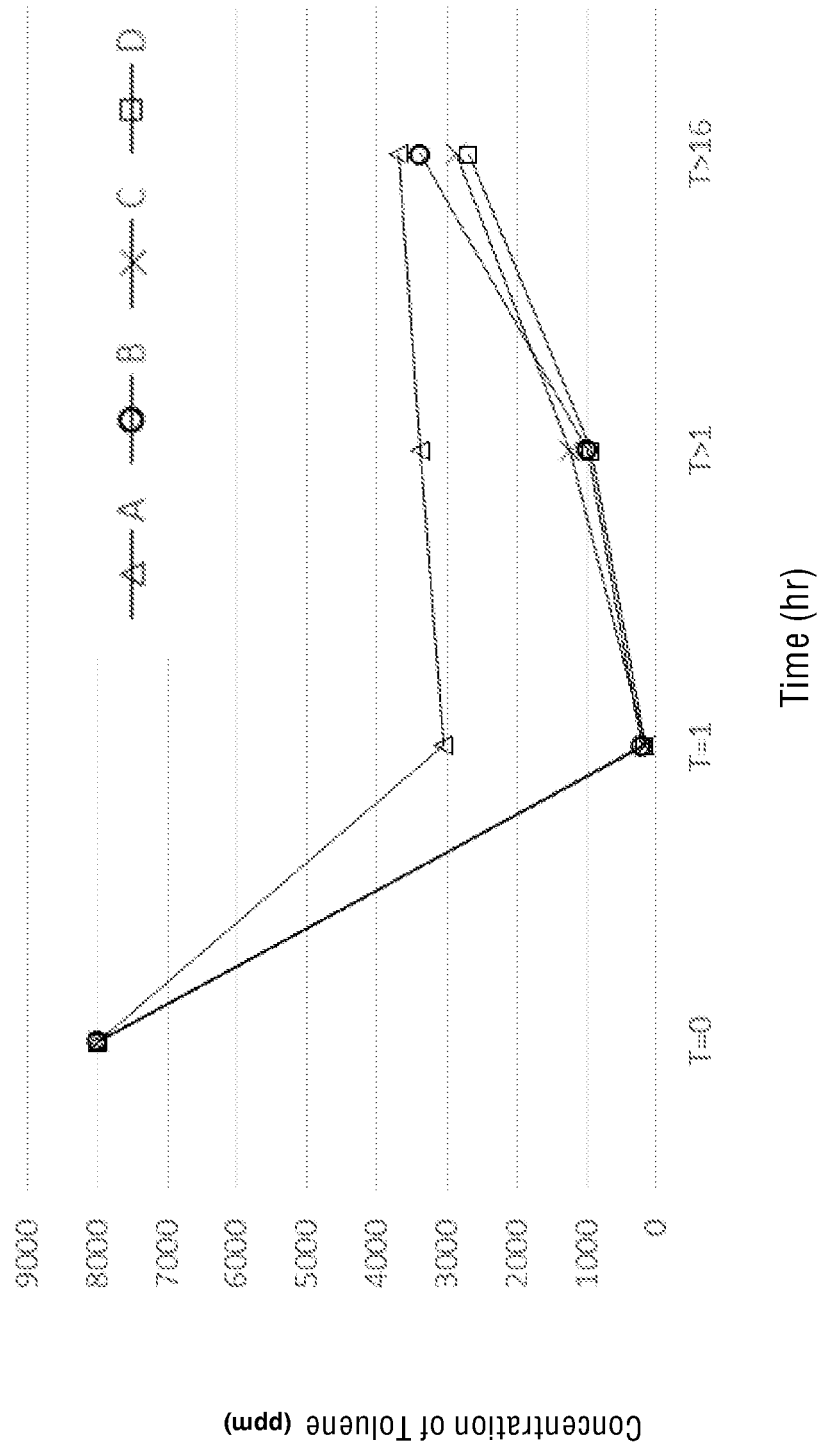

BIODEGRADABLE COMPOSITE AND PRODUCT CONTAINING BIODEGRADABLE COMPOSITE

BACKGROUND OF THE INVENTION

1. Technical Field

The present invention relates generally to a biodegradable composite, and more particularly to a biodegradable composite that is compostable and a product containing the biodegradable composite.

2. Description of Related Art

Nowadays, when life becomes more convenient, plastic garbage and waste are increased day by day. Even though some recycling companies do recycle plastic garbage and waste, plastic garbage and waste are too much to be recycled and to be decomposed. Therefore, plastic waste pollutes and damages the environment.

Recently, since plastic pollution is too serious, related companies try to develop biodegradable plastics which could be decomposed naturally to reduce the environmental burden. However, under a natural situation, biodegradable plastics need more than 300 days to be decayed completely. Therefore, within a short period of time, an efficacy of reducing the plastic waste by using the biodegradable plastics instead of normal plastics is not significant.

On the other side, generally, biowaste, including food waste, kitchen waste, animal and plant residues, and so on, could be composed to allow the biowaste to return to the natural environment. However, in fact, when the biowaste does not be properly processed (decomposed or fermented), an unpleasant odor, plant diseases, and pest outbreaks may occur. For example, when the biowaste is decayed under an anaerobic situation, organic acid, alcohol, ketone, sulfide (e.g. hydrogen sulfide, $H_2S$), nitride (e.g. skatole $C_9H_9N$ and ammonia $NH_3$), and other odor gases are possibly generated.

Except the odor gases generated during the decay of the biowaste, some other odor substances are existing in a normal environment, such as xylene and toluene that are generated during evaporation of an adhesive solvent, marsh gas that spreads from a sewer, cooking odor, rancid odor, and so on. Besides, during industrial manufacture, odor gases may be generated as well. For example, thiol, hydrogen sulfide, and/or amine gases may be generated during desulfurhydrogenation of petroleum, hydrodenitrification of petroleum, and degradation of resin.

Therefore, a biodegradable composite and a product containing the biodegradable composite, which could speed up the degradation of the biodegradable plastic to avoid unpleasant smells, are needed. Furthermore, the biodegradable composite and the product facilitate a decomposition process of the biowastes to form composts, so that the biowaste could be recycled, thereby achieving an ecofriendly and sustainable development goal.

BRIEF SUMMARY OF THE INVENTION

In view of the above, the primary objective of the present invention is to provide a biodegradable composite and a product containing the biodegradable composite, which could efficiently degrade the biodegradable plastic, effectively suppress bad odors, and facilitate the biowastes to be decomposed to form a biobased compost, thereby achieving environmental protection and circular economy.

The inventive subject matter provides a biodegradable composite, which could instantly deodorize and accelerates a decomposition process to form compost, including an organic matter and a porous material. The organic matter accounts for 40% to 80% of a weight of the biodegradable composite, wherein the organic matter includes viable bacteria and has a total plate count that is greater than or equal to $10^4$ CFU/g. The porous material accounts for 20% to 60% of the weight of the biodegradable composite.

The inventive subject matter further provides a product, which could instantly deodorize and accelerates a decomposition process to form compost and is adapted to contact a biological substrate. The product includes a biodegradable composite and a biodegradable plastic. The biodegradable composite includes an organic matter having viable bacteria and a porous material, wherein the organic matter accounts for 40% to 80% of a weight of the biodegradable composite, and a total plate count of the organic matter is greater than or equal to $10^4$ CFU/g. The porous material accounts for 20% to 60% of the weight of the biodegradable composite. The biodegradable composite accounts for less than or equal to 10% of a weight of the product. The biodegradable plastic is decomposable by biological activities and contacts with the biodegradable composite With such design, by utilizing the biodegradable composite and the product containing the biodegradable composite provided by the present invention, the speed of degradation of the biodegradable plastic could be enhanced. Additionally, the porous material of the biodegradable composite and the product has great absorption capability for absorbing the unpleasant odors, such as xylene and toluene of the solvent of the paint and the adhesive or other bad odors generated during the industrial manufacture. Therefore, the biodegradable composite and the product could prevent the effusion of the unpleasant odors and accelerate the degradation of the biowastes to form the biobased compost, thereby enhancing environmental protection and recycle.

BRIEF DESCRIPTION OF THE SEVERAL VIEWS OF THE DRAWINGS

The present invention will be best understood by referring to the following detailed description of some illustrative embodiments in conjunction with the accompanying drawing, in which FIG. 1 is a line graph, showing absorption of Volatile Organic Compounds (VOC) by each of the different composites of the comparative examples.

DETAILED DESCRIPTION OF THE INVENTION

A biodegradable composite of an embodiment of the present invention, which could instantly deodorize, be fast decomposed to form compost, includes an organic matter and a porous material. The organic matter accounts for 40% to 80% of a weight of the biodegradable composite, wherein the organic matter includes viable bacteria and has a total plate count that is greater than or equal to $10^4$ CFU/g; the porous material accounts for 20% to 60% of the weight of the biodegradable composite. In the current embodiment, the total plate count of the organic matter is $5 \times 10^7$ CFU/g to $5 \times 10^8$ CFU/g, which meets a standard of a total plate count of a microbial fertilizer. In the current embodiment, the organic matter accounts for 40% to 45% of the weight of the biodegradable composite, and the porous material accounts for 55% to 60% of the weight of the biodegradable composite. In another embodiment, the organic matter accounts for 60% to 70% of the weight of the biodegradable composite, and the porous material accounts for 30% to 40% of the weight of the biodegradable composite. In the current embodiment, a sum of a weight of the organic matter and a weight of the porous material is equal to the weight of the biodegradable composite.

In the current embodiment, the viable bacteria are selected from a group consisting of thermoduric bacteria, *Bacillus coagulans*, *Bacillus subtilis*, *Bacillus thuringiensis*, *Pseudomonas putida*, Actinobacteria, and a combination thereof.

In the current embodiment, the porous material is selected from a group consisting of activated carbon, eggshell powder, shell powder, bamboo charcoal powder, and a combination thereof. The porous material has porosity and is good at absorbing unpleasant odors emitted by paint solvent, adhesive solvent (e.g. xylene and toluene), or emitted during an industrial manufacture, so that the unpleasant odors could be prevented from spreading or escaping, thereby providing efficacy of deodorization. In the current embodiment, a weight ratio of the organic matter to the porous material is ranged from 0.6:1 to 1.2:1. In the current embodiment, each of pores of the porous material averagely contains 800 CFU to 1200 CFU of the viable bacteria per gram of the biodegradable composite. In the current embodiment, the biodegradable composite includes water that accounts for 1% to 3% of the weight of the biodegradable composite. In the current embodiment, a sum of the weight of the organic matter, the weight of the porous material, and a weight of the water is equal to the weight of the biodegradable composite.

An experiment mentioned below is designed for testing and illustrating how the volatile organic compounds (VOC) is affected by each of composites of multiple comparative examples, the result of the experiment is illustrated in FIG. 1. In this experiment, the VOC is toluene.

Composite of comparative example A is the organic matter having the viable bacteria, and the organic matter is 3 kg. Composite of comparative example B is activated carbon of 3 kg. Composite of comparative example C is a mixture that combines the organic matter containing the viable bacteria of 1.5 kg and activated carbon of 1.5 kg. Composite of comparative example D is the mixture of 3 kg mixed with water of 50 g, wherein the mixture combines the organic matter containing the viable bacteria of 1.5 kg and activated carbon 1.5 kg.

Put each of the composites of the comparative examples A to D in an environment with toluene, wherein an initial concentration of the toluene is 8000 ppm, and then observe and assess a toluene absorption capacity of each of the composites of the comparative examples A to D at different times, thereby comparing a deodorizing capacity of each of the composites of the comparative examples A to D.

TABLE 1

| Concentration of toluene (ppm) | Time to measure the toluene (VOC) | | | |
| --- | --- | --- | --- | --- |
| | T = 0 hr | T = 1 hr | T > 1 hr | T > 16 hr |
| Comparative example A | 8000 ppm | 3040 ppm | 3385 ppm | 3693 ppm |
| Comparative example B | 8000 ppm | 226 ppm | 998 ppm | 3385 ppm |
| Comparative example C | 8000 ppm | 159 ppm | 1232 ppm | 2870 ppm |
| Comparative example D | 8000 ppm | 169 ppm | 938 ppm | 2689 ppm |

As illustrated in table 1 and FIG. 1, as to the comparative example A, wherein the composite is the organic matter containing the viable bacteria. At the first hour after the composite of the comparative example A is put into the environment with toluene (T=1 hr), the concentration of toluene is 3040 ppm. Comparing with the comparative examples B to D, the toluene absorption capacity of the composite of the comparative example A is the worst among all the comparative examples.

Referring to the comparative examples B and C, the composite of the comparative example B is merely activated carbon. Comparing with the comparative example B, the composite of the comparative example C has the same weight and further includes the organic matter containing the viable bacteria. When the measuring times are between the first hour and the sixteenth hour (T>1 hr), the concentration of toluene of the comparative example C averagely is 1232 ppm, and the concentration of toluene of the comparative example B averagely is 998 ppm. The average concentration of toluene of the comparative example C is greater than that of the comparative example B. However, when the measuring times are between the sixteenth hour and the twenty-fourth hour (T>16 hr), the concentration of toluene of the comparative example C averagely is 2870 ppm and the concentration of toluene of the comparative example B averagely is 3385 ppm. The average concentration of toluene of the comparative example C is obviously smaller than that of the comparative example B. As a result, when the comparative example B and comparative example C have the same weight, the toluene absorption capacity of the composite the comparative example C is better than that of the comparative example B.

Furthermore, comparing with the comparative example C, the comparative example D further includes water, except the same mixture of the comparative example C. As illustrated in table 1 and FIG. 1, when the measuring times are between the first hour and the sixteenth hour (T>1 hr), the concentration of toluene of the comparative example C is 1232 ppm, and the concentration of toluene of the comparative example D is 938 ppm. The concentration of toluene of the comparative example D is smaller than that of the comparative example C. When the measuring times are between the sixteenth hour and the twenty-fourth hour (T>16 hr), the concentration of toluene of the comparative example D is 2689 ppm and the concentration of toluene of the comparative example C is 2870 ppm. The concentration of toluene of the comparative example D is obviously smaller than that of the comparative example C. As a result, the toluene absorption capacity of the composite of the comparative example D is better than that of the comparative example C.

A product of another embodiment according to the present invention is adapted to contact a biological substrate, wherein the product could deodorize instantly and be decomposed fast to form compost. The product includes the biodegradable composite mentioned above and a biodegradable plastic, wherein the biodegradable composite accounts for less than or equal to 10% of a weight of the product; the biodegradable plastic is decomposable by biological activities and contacts with the biodegradable composite.

In the current embodiment, the biodegradable plastic includes polylactic acid (PLA). In the current embodiment, the biodegradable plastic is mixed with the biodegradable composite.

In the current embodiment, the biodegradable plastic covers the biodegradable composite. In another embodiment, the biodegradable plastic encapsulates a part of the biodegradable composite, and the rest part of the biodegradable composite is attached to the biodegradable plastic. In the current embodiment, the product having the biodegradable composite could be a filter, a packaging material, a paper material, a cladding material, a package, a cladding structure, and a combination thereof.

In the current embodiments, the product has an identification code, wherein the identification code could be a two-dimensional code (QR code) and could be scanned by a user with a mobile communication device to connect to a blockchain for monitoring a location of the product. When the product is used and waste or garbage is produced, a related company could recycle the product by itself with an assistance of blockchain technology to manage the recycling. Furthermore, after the product is recycled, additional biodegradable composite is added to the recycled product to accelerate a decomposition process of the recycled product. The recycled product is decomposed by the biodegradable composite to form a biobased compost which could be used as a fertilizer. After the product is decomposed, other remained wastes could be filtered to collect useful substances for reuse, thereby enhancing benefits of a circular economy.

The biodegradable composite and the product containing the biodegradable composite provided by the present invention could accelerate the speed of the decomposition process of the biodegradable plastic, suppress bad odors, and facilitate the decomposition process of the biowaste to form the matured biobased compost, thereby achieving the eco-friendly and sustainable goal. Moreover, according to the experiment result of the present invention proves the comparative example including the organic matter containing the viable bacteria and the activated carbon has better toluene absorption capacity than the comparative example merely including the activated carbon when each of the comparative examples has the same weight. Additionally, when the composites of the two comparative examples have the same components (namely both are including organic matter containing the viable bacteria, the activated carbon), the comparative example with water has better toluene absorption capacity than the comparative example without water.

It must be pointed out that the embodiment described above is only a preferred embodiment of the present invention. All equivalent structures which employ the concepts disclosed in this specification and the appended claims should fall within the scope of the present invention.

What is claimed is:

1. A product adapted to contact a biological substrate, comprising:
   a biodegradable composite consisting of viable bacteria, a porous material, and water; and
   a biodegradable plastic that is decomposable by biological activities, covers and contacts with the biodegradable composite, wherein the biodegradable plastic comprises polylactic acid;
   wherein the product comprises less than or equal to 10% by weight of the biodegradable composite;
   wherein the viable bacteria accounts for 40% to 80% of a weight of the biodegradable composite, and a total plate count of the viable bacteria is greater than or equal to $10^4$ CFU/g;
   wherein the porous material is selected from a group consisting of activated carbon, egg-shell powder, shell powder, bamboo charcoal powder and a combination thereof; and accounts for 20% to 60% of the weight of the biodegradable composite;
   wherein the viable bacteria is solid and a weight ratio of the viable bacteria to the porous material is 1:1;
   wherein the viable bacteria are selected from the group consisting of thermoduric bacteria, *Bacillus thuringiensis, Pseudomonas putida*, Actinobacteria, and a combination thereof;
   wherein the water accounts for 1% to 3% of the weight of the biodegradable composite.

2. The product as claimed in claim 1, wherein the product comprises a filter, a packaging material, a paper material, a cladding material, a package, a cladding structure, or a combination thereof.

3. The product as claimed in claim 1, comprising an identification code.

4. A biobased compost comprising a biological substrate and the product as claimed in claim 1, wherein during a recycling process of the product, the recycled product contacts the biological substrate and an additional biodegradable composite is added to the recycled product to allow the recycled product to be decomposed by the biodegradable composite.

* * * * *